United States Patent [19]

Demarest et al.

[11] Patent Number: 5,532,226

[45] Date of Patent: Jul. 2, 1996

[54] TRIFLUOROMETHYBENZYLPHOSPHONATES USEFUL IN TREATING OSTEOPOROSIS

[75] Inventors: Keith Demarest, Flemington; Charles Schwender, Califon, both of N.J.; David Wustrow, Ann Arbor, Mich.

[73] Assignee: Ortho Pharmaceutical Corporation, Raritan, N.J.

[21] Appl. No.: 164,602

[22] Filed: Dec. 9, 1993

Related U.S. Application Data

[63] Continuation-in-part of Ser. No. 732,267, Jul. 18, 1991, Pat. No. 5,300,687.

[51] Int. Cl.⁶ ............................ C07F 9/02; C07F 9/28; C07D 279/12; A61K 31/66
[52] U.S. Cl. ..................... 514/134; 514/141; 558/214; 558/217; 564/15; 546/22; 546/23; 544/57; 544/157; 544/337
[58] Field of Search ...................... 564/15; 544/57, 544/157, 337; 546/22, 23; 558/214, 217; 514/141, 134

[56] References Cited

U.S. PATENT DOCUMENTS

| | | | |
|---|---|---|---|
| 2,917,533 | 12/1959 | Burger et al. | 514/141 |
| 3,363,032 | 1/1968 | Fitch | 514/141 |
| 4,610,807 | 9/1986 | Brinkwert et al. | 570/128 |
| 5,242,908 | 9/1993 | Peyman et al. | 514/107 |
| 5,300,687 | 4/1994 | Schwender et al. | 564/15 |

OTHER PUBLICATIONS

R. Hermant, et al., Systematic Study of a Series of Highly Fluorescent Rod–Shaped Donor–Acceptor Systems, *J. Am. Chem. Soc.* 1990, 112, 1214–1221.
Hermant et al., J. Am. Chem. Soc. (1990) 112, 1214–1221.
Terada et al, Chem. Abs. (1990) 112:235,189 p.
Brinkwerth, Chem. Abs. (1986) 104: 35,465y.

*Primary Examiner*—Matthew V. Grumbling
*Attorney, Agent, or Firm*—Ralph R. Palo

[57] ABSTRACT

Novel benzylphosphonate compounds of the general formula I:

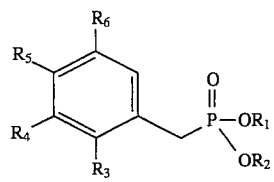

are disclosed as useful in treating bone wasting diseases including postmenopausal osteoporosis in increasing in mammals bone formation and bone mass.

12 Claims, No Drawings

TRIFLUOROMETHYBENZYLPHOSPHONATES USEFUL IN TREATING OSTEOPOROSIS

RELATED APPLICATIONS

This is a Continuation-In-Part of Ser. No. 732,267, filed Jul. 18, 1991 now U.S. Pat. No. 5,300,687.

BACKGROUND OF THE INVENTION

Osteoporosis is a bone-wasting disease in which there is an imbalance or uncoupling between the rate of bone formation and resorption resulting in a decrease; in total bone mass. As a result of this decrease in bone mass the skeleton becomes weakened and unable to bear the normal weight-bearing stresses. The effects of osteoporosis are generally seen in the weight-bearing part of the skeleton, especially the spine and hips, which can fracture in the absence of trauma. Osteoporosis affects about 24 million people in the United States and 200 million worldwide and is blamed for 2.5 million fractures a year in elderly women. The American Medical Association estimates that 25% of white women will suffer fractures of the hip or spine in their lifetime as a result of osteoporosis.

The current therapies for postmenopausal osteoporosis consist of treatments which are for the most part preventative; estrogen replacement, bisphosphonates, vitamin D metabolites and calcium supplements act to inhibit bone resorption associated with the onset of menopause. Estrogen replacement in these patients is quite effective in reducing further loss of bone mass but it does not induce an increase in bone mass which is needed to reduce fracture risk and pain. These treatments have little utility in the treatment of those patients with existing osteoporosis-induced loss of bone mass who have a high fracture risk and back/joint pain. Post-menopausal women with vertebral bone mass of less than 100 mg/cc would be considered below the "fracture threshold" and would be candidates for treatment with an agent which would increase bone mass and thereby restore lost bone. The present invention focuses on agents which are useful in treating bone wasting diseases by increasing an individuals bone mass and thus reducing or eliminating fracture risk. The therapeutic need for this type of agent is clearly present, especially when one considers the poor patient compliance associated with estrogen replacement therapies.

U.S. Pat. No. 4,610,807 disclosed diethyl 3-trifluoromethylbenzylphosphonate. The compound is not specifically claimed or characterized in the patent but apparently is used in situ as a crude synthetic intermediate towards unrelated compounds with non-medicinal use (fabric whitener). Acids were neither disclosed nor claimed in this reference. Isomeric ortho and para trifluoromethylbenzylphosphonates are similarly disclosed as the esters.

U.S. Pat. No. 2,917,533 discloses several substituted benzylphosphonic acids and esters with utility claims of antihistaminic, antibacterial and herbicidal or plant growth regulatory activity. No 3-$CF_3$ analog is described.

SUMMARY OF THE INVENTION

Novel benzylphosphonate compounds of the general formula I:

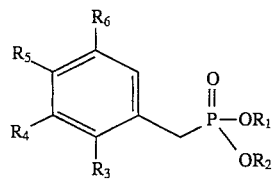

wherein $R_1$, $R_2$, $R_3$, $R_4$, $R_5$ and $R_6$ are defined hereinafter have been found to have utility to treat bone wasting diseases including osteoporosis through enhancement of bone calcification, rather than traditional approaches which generally involve inhibition of bone degradation or resorption. The invention is also directed to pharmaceutical compositions containing the compounds of formula I and the methods of treating osteoporosis by administering such compounds and compositions.

DETAILED DESCRIPTION OF THE INVENTION

The present invention is directed to compounds of formula I:

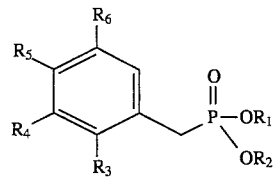

wherein $R_1$ and $R_2$ are the same or different and are selected from any of hydrogen, $C_1$–$C_8$ alkyl, $C_1$–$C_8$ alkenyl, hydroxyalkyl wherein the alkyl portion is $C_1$–$C_8$, alkoxyalkyl wherein the alkyl portion is $C_1$–$C_8$, aralkyl wherein the alkyl portion is $C_1$–$C_8$, such as benzyl, phenylethyl, phenylpropyl, aryl such as phenyl or aminoalkyl. Aminoalkyl includes substituents of the formula —(CH2)n—$NR_7R_8$, wherein n=2–6 and $R_7$ and $R_8$ are the same or different and are selected from any of H, $C_1$–$C_4$ alkyl, aralkyl wherein the alkyl portion in $C_1$–$C_4$ or $R_7$ and $R_8$ may be taken together to form a heterocyclic ring having from 5 to 7 ring atoms containing one or more heteroatoms such as N, O and S. Examples of suitable ring systems include piperidino, morpholino, tetrahydroquinolinyl, tetrahydro-isoquinolinyl, thiomorpholino and piperazino substituted at the N-4 position by $R_9$, wherein $R_9$ is selected from any one of $C_1$–$C_4$ alkyl, or aralkyl wherein the alkyl portion is $C_1$–$C_4$ alkyl or phenyl.

$R_3$ and $R_5$ may each be either H or $CF_3$, with the proviso that only one of $R_3$ or $R_5$ may be $CF_3$ at the same time. $R_4$ and $R_6$ may each be H or $CF_3$, with the proviso that if either or both of $R_4$ and $R_6$ are $CF_3$, neither $R_3$ nor $R_5$ may be $CF_3$ and with the further proviso that $R_3$–$R_6$ may not each be H at the same time.

As used herein the terms "alkyl", "alkenyl" and "alkoxy" when used alone or together with another moiety include both straight and branched alkyl groups.

The term "aryl", as used herein alone or in combination with other terms, indicates aromatic hydrocarbon groups such as a phenyl or naphthyl group. The term "aralkyl" indicates a radical containing a lower $C_1$–$C_8$ alkyl group substituted with an aryl radical.

The compounds of the present invention may also be in the form of pharmaceutically acceptable salts such as sodium, potassium, arginine, lysine, alkyl ammonium such as cyclohexylamine and tris(hydroxyethyl)amine. Basic esters may also be in the form of salts such as hydrochloric, hydrobromic p-toluenesulfonate mesylate, and organic acids such as fumarate.

According to the present invention the compounds may be prepared according to the following general reaction schemes:

REACTION SCHEME

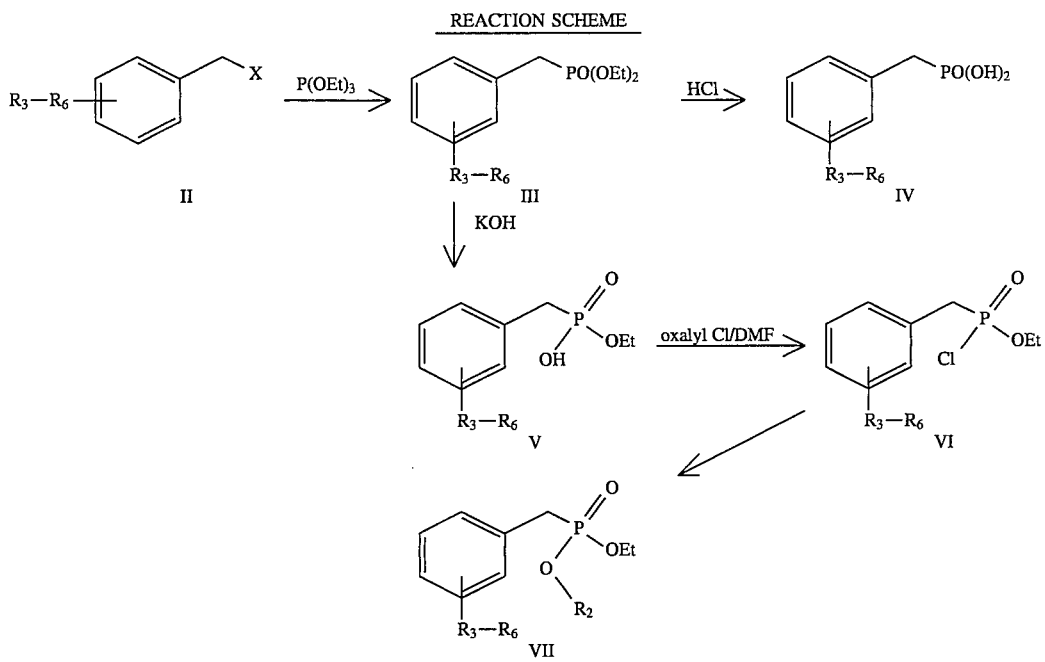

As shown, the starting material, a trifluorohalide wherein X is either chloro or bromo and $R_3$, $R_4$, $R_5$ and $R_6$ are as defined herein is reacted with trialkyl phosphite, under temperatures of about 50° C.–200° C. to give an alkyl trifluorobenzyl phosphonate of formula III. Hydrolysis using an acid such as hydrochloric acid or other suitable acids such as $(CH_3)_3SiBr$, HBr, or $BBr_3$ is used to give the free phosphonic acid of formula IV. Alternatively, the compound of the formula III may be reacted with a base such as potassium or sodium hydroxide, to give the corresponding mono acid product of formula V. Conversion of this mono acid to the acid chloride of formula VI may be accomplished using oxalyl chloride and dimethylformamide or $PCl_5$. The mixed diester of formula VII may than be prepared from the acid chloride of formula VI by reacting the compound of formula VI with the appropriate alcohol such as diethylaminoethanol, 3-phenylpropanol, hydroxyethylmorpholine, methoxyethanol, ethylene glycol and other well known alcohols.

To prepare the pharmaceutical compositions of this invention, a compound of formula I, as the active ingredient is mixed with a pharmaceutical carrier according to conventional pharmaceutical compounding techniques, which carrier may take a wide variety of forms depending on the form of preparation desired for administration, e.g.; oral, by suppositories, injectable, or parenteral. In preparing the compositions in oral dosage form, any of the usual pharmaceutical media may be employed. Thus, for liquid oral preparations, such as, for example; suspensions, elixirs and solutions, suitable carriers and additives include water, glycols, oils, alcohols, flavorants, perservatives, coloring agents and the like. For solid oral preparations such as, for example; powders, capsules and tablets, suitable carriers and additives include, starches, sugars, diluents, granulating agents, lubricants, binders, disintegrating agents, and the like. Because of their ease of administration, tablets and capsules represent the most advantageous oral dosage unit form in which case, solid pharmaceutical carriers are obviously employed. If desired, tablets may be sugar coated or enteric coated by standard techniques. For suppositories, the carrier will usually comprise cocoa butter. For parenterals, the carrier will usually comprise sterile water, though other ingredients, for example; for purposes such as aiding solubility or for preservation, may be included. Injectable suspensions may also be prepared, in which case appropriate liquid carriers, suspending agents and the like may be employed. The pharmaceutical compositions herein will contain, per unit dosage unit, e.g., tablet, capsule, powder, injection, suppository, teaspoonful and the like, from about 0.1–100 mg/kg. The use of either continuous daily administration or post-periodic dosing may be employed.

The following examples illustrate the present invention but are not deemed to be limiting. Examples 1,2, 3 and 5–14 illustrate compounds of the present invention. Example 4 illustrates the preparation of an intermediate used to obtain any of the compounds of Example 5, 6 and 7.

EXAMPLE 1

Diethyl 3-trifluoromethylbenzylphosphonate

A mixture of 3-trifluoromethylbenzyl bromide (5.74 g, 24.0 mmol) and triethyl phosphite ( 4.98 g, 30 mmol) was heated at reflux under nitrogen for 3 hours. The excess triethyl phosphite was removed by distillation and the crude product obtained was distilled at 140°–145° C. at 4 mm to yield 6.44 g (90.7%) of analytically pure product as a clear liquid. 300 MHz $^1$H NMR (CDCl$_3$): δ, 3.20 (d,2H J=21.78 Hz, PCH2). D.C.I.M.S.[MH$^+$, 297].

EXAMPLE 2

3-Trifluoromethylbenzylphosphonic acid

Diethyl 3-trifluoromethylbenzylphosphonate (3.0 g, 10.0 mmol) was dissolved in a mixture; of 50 mL of conc hydrochloric acid and 1.5 mL of EtOH and was heated at reflux for 17 hours. After cooling the clear reaction mixture in an ice-water mixture, the white crystalline solid which formed was collected to give 2.05 g (84.3%) of the analytical product, mp=163°–164° C. 300 MHz $^1$H NMR (DMSO-D6) δ, 7.40–7.75 (m, 4H, aromatic), 3.09 (d, 2H, J=21.5 Hz, PCH$_2$). D.C.I.M.S.[MH$^+$, 241].

EXAMPLE 3

Ethyl 3-trifluoromethylbenzylphosphonic acid

The diethyl 3-trifluoromethylbenzylphosphonate (10.0 g, 34.0 mmol) was dissolved in a mixture of 300 mL of 75% aqueous ethanol and 18.9 g of KOH and the resultant mixture was heated at reflux for 3 hours. The reaction mixture was poured into H$_2$O, acidified with hydrochloric acid, and extracted with CHCl$_3$ (3×500 mL). The chloroform extract was dried with anhydrous Na$_2$SO$_4$ and evaporated to yield 8.64 g (94.7%) of white solid product, mp=48°–51° C.; D.C.I.M.S.[MH$^+$, 269].

EXAMPLE 4

3-Trifluromethylbenzylphosphonochloridic acid ethyl ester

Ethyl 3-trifluoromethylbenzylphosphonic acid, (7.46 mmol) was dissolved in 15 mL of CH$_2$Cl$_2$ and cooled to 0° C. under nitrogen. After the oxalyl chloride (0.95 g, 7.46 mmol) had been added, 0.03 mL of DMF was slowly added in 3 portions, and the resultant mixture was stirred at room temperature for 3 hours. Evaporation in vacuo gave the crude chloride which was used without further purification.

EXAMPLE 5

Allyl ethyl 3-trifluoromethylbenzylphosphonate

The 3-trifluoromethylbenzylphosphonochloridic acid ethyl ester of Example 4 (0.2 g, 0.7 mmol) was dissolved in 20 mL of CH$_2$Cl$_2$ and added slowly at 0° C. to a mixture of 1.0 mmol of allyl alcohol and 1.0 of mmol triethylamine in 20 mL of CH$_2$Cl$_2$. The reaction mixture was stirred for 5 hours and then diluted with H$_2$O. The aqueous phase was further extracted 3 times with CH$_2$Cl$_2$. The organic extracts were combined and, after drying with anhydrous Na$_2$SO$_4$, were evaporated to give the crude product as an oil. Purification by column chromatography on silica gel using ethyl acetate/hexane (2.5:1) yielded 0.14 g (63%) of analytically pure product as a colorless oil. D.C.I.M.S.[MH$^+$, 309].

EXAMPLE 6

Diethylaminoethyl ethyl 3-trifluoromethylbenzylphosphonate

Ethyl 3-trifluoromethylbenzylphosphonic acid, (7.55 g, 28 mmol) was dissolved in 100 mL of CH$_2$Cl$_2$ and cooled to 0° C. under nitrogen. After the oxalyl chloride (28 mmol) had been added, 0.5 mL of DMF was slowly added in 3 portions, and the resultant mixture was stirred at room temperature for 3 hours. Evaporation in vacuo gave the crude acid chloride which was dissolved in 90 mL of CH$_2$Cl$_2$ and added dropwise to a mixture of N,N-diethylaminoethanol (3.29 g, 28 mmol) and triethylamine (3.42 g, 34 mmol) in 60 mL of CH$_2$Cl$_2$ cooled at 0° C. The resultant mixture was allowed to warm to room temperature and stirred for 4 hours. Water was added (100 mL) and the aqueous phase was extracted 3 times with CH$_2$Cl$_2$. The combined organic extracts were dried with anhydrous Na$_2$SO$_4$, and evaporated to give the crude product as an oil. Purification was accomplished through column chromatography on silica gel using CH$_2$Cl$_2$ containing 2% MeOH and 0.1% NH$_3$ and gave 1.1 g of the analytical product as an orange oil. D.C.I.M.S.[MH$^+$, 368].

EXAMPLE 7

Ethyl 3-phenylpropyl 3-trifluoromethylbenzylphosphonate 3-trifluoromethylbenzylphosphonic acid mono ethyl ester (1.5 g, 5.6 mmol) was dissolved in 20 mL of CH$_2$Cl$_2$ and cooled to 0° C. under nitrogen. After the oxalyl chloride (8.46 mmol) had been added, 0.04 mL of DMF was slowly added in 3 portions, and the resultant mixture was stirred at room temperature for 3 hours. Evaporation in vacuo gave the crude acid chloride which was used without further purification. 3-Phenyl-1-propanol (0.76 g, 5.6 mmol), in 15 mL of CH$_2$Cl$_2$, was added to a cold mixture of crude chloro ethyl 3-trifluoromethylbenzylphosphonate (5.6 mmol), triethylamine (0.85 g, 8.4 mmol), and CH$_2$Cl$_2$ (20 mL) cooled at 0° C. The resultant reaction mixture was allowed to stir at room temperature for 4 hours. Evaporation of the volatile components gave a quantitative yield of the expected product. Purification by column chromatography (silica gel, 25% ethyl acetate/hexane) gave 1.66 g (52.3%) of analytically pure product as a pale yellow oil. D.C.I.M.S.[MH$^+$, 387].

EXAMPLE 8

Diethyl 4-trifluoromethylbenzylphosphonate

A mixture of 4-trifluoromethylbenzyl bromide (5.68 g, 23.8 mmol) and triethyl phosphite (10.4 g, 63 mmol) was heated at reflux under nitrogen for 5 hours. The excess triethyl phosphite was removed by distillation and the crude product was purified by distillation at 95° C. (0.07 mm Hg.) to give 6.27 g, 89% of the product as an oil. D.C.I.M.S. [MH$^+$, 297].

EXAMPLE 9

4-Trifluoromethylbenzylphosphonic acid

The diethyl 4-trifluoromethylbenzylphosphonate (3.0 g, 10 mmol) was dissolved in a mixture of 50 mL of conc hydrochloric acid and 5 mL of EtOH and heated at reflux for 17 hours. After cooling the mixture in an ice bath, white crystalline material was collected. Recrystallization of the solid from H$_2$O gave 1.80 g, 75% of the analytically pure product: mp=163°–164° C.; D.C.I.M.S. [MH$^+$, 241].

EXAMPLE 10

Diethyl 2-trifluoromethylbenzylphosphonate

A mixture of 2-trifluoromethylbenzyl chloride (2.0 g, 10.0 mmol) and triethyl phosphite (2.13 g, 13 mmol) was heated at 160° C. under nitrogen for 3 hours. The excess triethyl phosphite was removed by distillation and the crude product obtained was distilled at 87°–90° C. (0.05 mm Hg) and isolated as a colorless oil; yield, 1.68 g, 56.8%; D.C.I.M.S. [MH$^+$, 297].

EXAMPLE 11

2-Trifluoromethylbenzylphosphonic acid

The diethyl 2-trifluoromethylbenzylphosphonate (1.22 g, 4.12 mmol) was dissolved in a mixture of 50 mL of conc hydrochloric acid and 5 mL of EtOH and was heated at reflux temperature for 17 hours. After cooling the mixture in an ice bath, white crystalline acid was collected to give 0.46 g, 46% of the desired product, mp=190°–192° C.; D.C.I.M.S. [MH$^+$, 241].

EXAMPLE 12

Diethyl 3.5-bis(trifluoromethyl)benzylphosphonate

A mixture of 3,5-bis-trifluoromethylbenzyl bromide (5.0 g, 16 mmol) and triethyl phosphite (3.4 g, 20 mmol) was heated at 160° C. for 20 hours. The reaction mixture was cooled and distilled at 83° C. (0.03 mm Hg) to give 2.36 g of the product as a colorless oil in 48% yield. D.C.I.M.S. [MH$^+$, 365].

EXAMPLE 13

3.5-Bis(trifluoromethyl)benzylphosphonic acid

Diethyl 3,5-bis(trifluoromethyl)benzylphosphonate (1.0 g, 2.7 mmol)in 15 mL of conc hydrochloric acid and 0.5 mL of ethanol was heated at reflux for 72 hours. The mixture was evaporated to an oily residue which crystallized upon standing to give 0.41 g of the product (49% yield) the as a white solid: mp. 206°–208° C.; D.C.I.M.S. [MH$^+$, 309].

EXAMPLE 14

Ethyl morpholinoethyl 3-trifluoromethylbenzylphosphonate

3-Trifluoromethylbenzylphosphonochloridic acid ethyl ester (7.0 mmol)in 20 mL of CH$_2$Cl$_2$ is added slowly to a mixture of N-(2-hydroxyethyl)morpholine and triethylamine (7 mmol) in 20 mL of CH$_2$Cl$_2$ cooled in an ice bath. The resultant mixture is allowed to reach room temperature and is stirred for 5 hours. Water is added (100 mL) and the aqueous phase is extracted 3 times with CH$_2$Cl$_2$ (3×100 mL). The combined organic extracts are dried with anhydrous MgSO$_4$, and evaporated to give the desired product.

Compounds of the present invention have utility to treat bone wasting diseases including osteoporosis through enhancement of bone calcification rather than traditional approaches which generally involve inhibition of bone degeneration or resorption. The compounds of the present invention have been evaluated as stimulators of proliferation of osteoblast cell culture which is predictive of enhancement of bone mass and bone formation in vive and the compound of Example 2 has been evaluated in in vivo screens which evidence the enhancement of bone mass and bone formation.

Osteoblast cell proliferation

The action of select compounds to stimulate osteoblast growth can be measured in culture by estimating the rate of DNA synthesis by the rate of $^3$H-thymidine incorporation into DNA. Only cells undergoing mitosis will synthesize new DNA and thus only these cells will incorporate the radiolabelled DNA-specific thymidine. The stimulation of the proliferation and differentiation of bone-forming cells, osteoblasts, is a prerequisite for an increase in bone formation and bone mass. The ability of agents to increase osteoblast proliferation and differentiation can be predicted by their action on cultured osteoblast-line cells in vitro. In this test, mouse (MC3T3-E 1) cloned by Sudo et al. Koriyama, Japan) and human (TE-85) osteoblast-line cells (American Type Tissue Culture Collection, #CRL 1543, Rockville, Md.) were cultured in vitro and the effect of various agents was tested on osteoblast cell proliferation. Osteoblasts were isolated and cultured according to literature methods. [J. E. Puzas, R. H. Drivdahl, A. G. Howard, and D. J. Baylink, *Proc. Sec. Exper. Biol. Med.*, 166, 113–122, 1981]. Cells were harvested from large culture flasks where they were allowed to grow to near confluency using trypsin. The cells were plated into 96 well culture plates, 1600 cells in 100 µL per well in Dulbencos Modified Eagle's Medium with 25 mM HEPES buffer, L-glutamine (584 mg/L); D-glucose (4.5 g/L) supplemented with fetal bovine sera (10%); penicillin ( 100 units/mL) and streptomycin ( 100 mcg/mL); sodium pyruvate ( 10 µM final concentration). The cells were allowed to plate overnight in DMEM containing 10% fetal bovine sera at 37° C., in an atmosphere of 5% CO$_2$/95% air. Following their placement into 96 ell culture plates all the osteoblast-line cells, either the MC3T3-E 1 or the TE-85 cell lines, were allowed an additional 24 hours preincubation period in media containing only 0.1% fetal bovine sera. The next clay the test compounds were added and screened at concentrations ranging from 10$^{-4}$ to 10$^{-8}$ M depending on the study. Twenty hours later, a 20 µL aliquot of media containing 0.4 µCi of $^3$H-thymidine was added to each culture well. The cells were then incubated an additional 4 hours. The incubation was terminated by aspirating the media and washing with HBSS (Hank's Balanced Salt Solution). The cells were then treated with 100 µL of 0.5% trypsin and 5.3 mm of EDTA for 30 minutes at room temperature. The cells were then aspirated onto a glass fiber filter and washed with water. The radioactivity on the filters was quantified by liquid scintillation spectroscopy. The rate of $^3$H-thymidine incorporation into DNA is then utilized as an index of cell proliferation. The results are shown in Table 1 expressed as % times control where control is 100%.

TABLE I

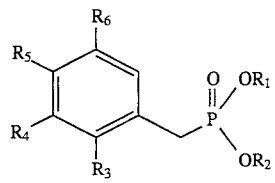

| Ex. | $R_1$ | $R_2$ | $R_3$ | $R_4$ | $R_5$ | $R_6$ | FORMULA | M.P./B.P. |
|---|---|---|---|---|---|---|---|---|
| 1 | Ethyl | Ethyl | H | $CF_3$ | H | H | $C_{12}H_{16}F_3O_3P$ | bp 140–145 (4 mm Hg) |
| 2 | H | H | H | $CF_3$ | H | H | $C_8H_8F_3O_3P$ | 163–164 |
| 3 | H | Ethyl | H | $CF_3$ | H | H | $C_{10}H_{12}F_3O_3P$ | 48–51 |
| 5 | Allyl | Ethyl | H | $CF_3$ | H | H | $C_{13}H_{16}F_3O_3P$ | colorless oil |
| 6 | Ethyl | $CH_2CH_2N(Et)_2$ | H | $CF_3$ | H | H | $C_{16}H_{20}F_3NO_3P$ | oil |
| 7 | Ethyl | $CH_2CH_2CH_2C_6H_5$ | H | $CF_3$ | H | H | $C_{19}H_{22}F_3O_3P$ | oil |
| 8 | Ethyl | Ethyl | H | H | $CF_3$ | H | $C_{12}H_{16}F_3O_3P$ | oil |
| 9 | H | H | H | H | $CF_3$ | H | $C_8H_8F_3O_3P$ | 163–164 |
| 10 | Ethyl | Ethyl | $CF_3$ | H | H | H | $C_{12}H_{16}F_3O_3P$ | colorless oil |
| 11 | H | H | $CF_3$ | H | H | H | $C_8H_8F_3O_3P$ | 190–192 |
| 12 | Ethyl | Ethyl | H | $CF_3$ | H | $CF_3$ | $C_{13}H_{15}F_6O_3P$ | colorless oil |
| 13 | H | H | H | $CF_3$ | H | $CF_3$ | $C_9H_7F_6O_3P$ | 206–208 |

| Ex. | [MH+] | Osteoblast Polif. % Control | | | |
|---|---|---|---|---|---|
| | | 1 µM | 0.1 µM | 0.01 µM | 0.001 µM |
| 1 | 297 | 78 | 127 | 124 | 159 |
| 2 | 241 | 299 | 337 | 240 | 232 |
| 3 | 269 | 94 | 117 | 120 | 132 |
| 5 | 309 | 113 | 118 | 127 | 127 |
| 6 | 368 | 84 | 102 | 97 | 101 |
| 7 | 387 | 92 | 113 | 106 | 114 |
| 8 | 297 | 108 | 100 | 78 | 60 |
| 9 | 241 | 195 | 154 | 155 | 149 |
| 10 | 297 | 100 | 97 | 161 | 193 |
| 11 | 241 | 77 | 103 | 102 | 116 |
| 12 | 365 | 299 | 337 | 240 | 231 |
| 13 | 309 | — | — | — | — |

Alkaline Phosphatase Production in Osteoblast-Like Cell in vitro

An index of osteoblast proliferation and differentiation is the production of alkaline phosphatase. Differentiated osteoblast secrete alkaline phosphatase as a secretory product. The compound of Example 2 (Compound #2) and sodium fluoride were tested for their ability to stimulate alkaline phosphatase activity in TE-85 osteoblast-line cells. TE-85 osteoblast-line cells were plated into 24 well plates (20,000 cells/well) in DMEM with 10% FBS. The following day the media is replaced with sera-free DMEM. This media is replaced 24 h later with DMEM containing 0.2% FBS and Compound #2, sodium fluoride, or sodium chloride in concentrations ranging from 0.01 µM to 100 µM. At 72 h the cells were, washed twice with Hanks buffered saline and extracted in 0.5 ml 1% Triton X-100 in water. Alkaline phosphatase activity was determined by measuring the rate of conversion of p-nitrophenolphosphate to p-nitrophenol (PNP) formation with a spectrophotometer. The data are then expressed as units activity/L (1 unit=1 umole PNP/min). Values represent the mean ±S.E. of alkaline phosphatase activity measured in 8 wells expressed as mU/l. Sodium fluoride treatment increased alkaline phosphatase activity in the TE85 osteoblasts. Concentrations between 0.1 and 10 µM had a significant effect on the cells. The same concentrations of another salt, sodium chloride had no effect. Treatment with Compound #2 increased the alkaline phosphatase activity in the TE85 osteoblasts in a dose-related fashion. Cells exposed to concentrations of 1 µM or greater showed significant elevations in enzyme activity as shown below. These results suggest that both sodium fluoride and Compound #2 stimulate alkaline phosphatase activity in osteoblast-line cells in culture. The results are shown in TABLE 2.

TABLE 2

EFFECT OF COMPOUND #2 ON ALKALINE PHOSPHATASE ACTIVITY IN HUMAN OSTEOBLAST-LINE CELLS (TE-85)

| | CONCENTRATION (uM) | | | | | |
|---|---|---|---|---|---|---|
| | VEHICLE | 0.01 | 0.1 | 1.0 | 10 | 100 |
| NaF | 2.21 ± 0.15 | 2.58 ± 0.15 | 3.01* ± 0.16 | 3.42* ± 0.10 | 3.07* ± 0.17 | 2.57 ± 0.21 |
| NaCl | — | 2.02 ± 0.07 | 2.00 ± 0.12 | 2.04 ± 0.12 | 2.24 ± 0.10 | 2.00 ± 0.10 |
| CP #2 | 2.12 ± 0.11 | 2.57 ± 0.22 | 2.62 ± 0.18 | 2.70* ± 0.11 | 2.71* ± 0.10 | 2.92* ± 0.08 |

*Value greater than vehicle, $p < 0.05$.

Biochemical Index (Alkaline Phosphatase) of Bone Formation in Mice

The ability or Compound #2 to stimulate indices of bone formation was tested in adult female mice by measuring changes in skeletal alkaline phosphatase in the skull as an index of bone formation. Adult CD female mice (20/group) were administered either Compound #2 (0.0001, 0.001, 0.01, 0.1 and 1.0 mg/kg) or vehicle (0.5% methocellulose) orally for 4 weeks. Skeletal alkaline phosphatase was extracted from the frozen mouse calvaria with 0.01% Triton X-100 in 0.3M KCI. Alkaline phosphatase activity was determined by measuring the rate of conversion of p-nitrophenolphosphate to p-nitrophenol (PNP) formation with a spectrophotometer. Values represent the mean ±S.E. of skeletal alkaline phosphatase activity expressed as units activity/mg calvaria weight. Skeletal alkaline phosphatase activity increased in response to treatment of Compound #2 (TABLE 3) suggesting a stimulation of bone formation.

TABLE 3

EFFECT OF COMPOUND #2 ON SKELETAL ALKALINE PHOSPHATASE IN MICE FOLLOWING 4 WEEKS OF TREATMENT

| | DOSE, MG/KG/DAY P.O. | | | | | |
|---|---|---|---|---|---|---|
| VEHICLE | 0.0001 | 0.001 | 0.01 | 0.1 | 1.0 |
| 9.00± 0.57 | 8.15± 0.41 | 8.95± 0.42 | 12.80 ± 1.20* | 11.64 ± 0.71* | 9.24± 0.77 |

*Value greater than vehicle, $p < 0.05$.

Osteocalcin As A Biochemical Index of Bone Formation Following 14 Days of Treatment in Female Rats Studies were undertaken to determine the acute effect of Compound #2 in the aged rat on several indices of bone formation. In this study, adult Sprague-Dawley retired female rats were administered Compound #2 (10 mg/kg in 0.5% methylcellulose vehicle) orally for 14 days. Blood was collected on the day of euthanasia for measurement of serum Osteocalcin expressed as ng/ml sera. Each value represents the mean ±1 S.E.M. of determinations from 15 animals. Serum osteocalcin was significantly increased only after 14 days of treatment suggesting a stimulation of bone formation. The results are shown in Table 4.

TABLE 4

Compound #2 (10 MG/KG. PO) ON OSTEOCALCIN AS AN INDICE OF BONE FORMATION FOLLOWING 14 DAYS OF TREATMENT IN THE FEMALE RAT

| | CONTROL | 14 DAYS |
|---|---|---|
| Serum Osteocalcin ng/ml | 11.60 ± 0.60 | 14.63* ± 0.86 |

*Value significantly greater than control value ($p < 0.05$).

Skeletal Alkaline Phosphatase as an Index of Bone Formation. Following 4 weeks of Treatment in Female Rats A dose-response for the effect of Compound #2 on skeletal alkaline phosphatase following 4 weeks of treatment was determined (TABLE 5).

Adult Sprague-Dawley retired female rats (Charles Rivers Labs, Portage, Me.) 8–9 months of age were administered Compound #2 (0.3, 3.0 and 30 mg/kg in 0.5% methylcellulose vehicle) orally for 4 weeks. Parietal bones of skull were extracted with 0.01% Triton X-100 in 0.3M KCI and alkaline phosphatase enzyme activity was quantitated by measuring the rate of conversion of p-nitrophenolphosphate to p-nitrophenol (PNP) expressed as uM PnP/mg calvaria/h.

TABLE 5

Compound #2 ON ALKALINE PHOSPHATASE FOLLOWING 4 WEEKS OF TREATMENT IN THE FEMALE RAT

| | VEHICLE | 0.3 MG/ KG | 3.0 MG/ KG | 30 MG/ KG |
|---|---|---|---|---|
| Skeletal Alk Phosphatase uM/PnP/mg | 60.02± 7.79 | 93.92*± 7.69 | 94.53± 10.12 | 105.14*± 13.64 |

*Value significantly greater than control value ($p < 0.05$).

Bone Mineral Content and Biochemical Indices of Bone Formation and Resorption Following 26 weeks of Treatment in Female Beagle Dogs The effect of Compound #2 on bone mineral content in intact female beagle dog was examined. Adult intact female dogs were dosed orally for 6 months with either vehicle or Compound #2 (0.3, 3.0, or 30 mg/kg). The effect of Compound #2 on the bone mineral content on the femoral neck (TABLE 6) and of the lumbar spine (TABLE 7) was determined by dual x-ray absorptometry following 3 and 6 months of treatment. A significant increase in bone mineral content of the neck of the femur was observed after 6 months of treatment with all doses examined. The largest increase, 5.0% over vehicle, was observed at the 0.3 mg/kg dose. Although the bone mineral content of the femoral neck tended to increase after 3 months of treatment, these observed differences were not statistically significant. The bone mineral content of the lumbar spine (AP spine; TABLE 7) did not change significantly following treatment with Compound #2 following either 3 or 6 months of treatment.

More specifically, in connection with the femoral neck study, adult female beagle dogs (15–16/treatment group) were administered either vehicle (0.5% methylcellulose, 1 ml/kg) or Compound #2 (0.3, 3.0, and 30 mg/kg) orally for 6 months. Bone mineral content was measured prior to the onset of dosing, after 3 and 6 months of treatment by dual energy X-ray absorptiometry using a XR-26 Norland instrument. The bone mineral content of the femur was determined by using the General scan analysis package to scan the neck of the femur (femoral neck) at settings of 1.0×1.0 mm pixel size at a scan speed of 45 mm/sec. Duplicate femoral neck bone mineral content measurements was taken at pretreatment, 3 months and 6 months of treatment. The duplicate determinations of BMC measurements at each time period were averaged and the 3 and 6 month data expressed as a percent change for each animal. The results are shown in TABLE 6.

TABLE 6

COMPOUND #2 ON BONE MINERAL CONTENT IN THE FEMORAL NECK FOLLOWING 3 AND 6 MONTHS OF TREATMENT IN THE FEMALE BEAGLE DOG

| | VEHICLE | 0.3 MG/ KG | 3.0 MG/ KG | 30 MG/ KG |
|---|---|---|---|---|
| MONTH 3 | | | | |
| % | 0.5% | 3.5% | 1.5% | 3.7% |

TABLE 6-continued

COMPOUND #2 ON BONE MINERAL CONTENT IN THE FEMORAL NECK FOLLOWING 3 AND 6 MONTHS OF TREATMENT IN THE FEMALE BEAGLE DOG

|  | VEHICLE | 0.3 MG/KG | 3.0 MG/KG | 30 MG/KG |
|---|---|---|---|---|
| BASELINE |  |  |  |  |
| (95% Confid Int) | (−3.0,4.1) | (1.1,6.0) | (−1.6,4.6) | (1.0,6.4) |
| Δ VEHICLE | — | 3.0% | 1.0% | 3.2% |
| (95% Confid Int) |  | (−1.3,7.3) | (−3.7,5.7) | (−1.2,7.6) |
| P-value | — | 0.0858 | 0.3383 | 0.0770 |
| MONTH 6 |  |  |  |  |
| % BASELINE | 0.2% | 5.2% | 4.7% | 5.6% |
| (95% Confid Int) | (−3.0,3.6) | (2.9,7.5) | (1.2,8.2) | (1.4,9.8) |
| Δ VEHICLE | — | 5.0% | 4.5% | 5.4% |
| (95% Confid Int) |  | (0.9,9.1) | (−0.4,9.4) | (0.0,10.8) |
| P-value | — | 0.0084 | 0.0359 | 0.0770 |

As regards to lumbar spine study, adult female beagle dogs (15–16/treatment group) were administered either vehicle (0.5% methylcellulose, 1 ml/kg) or Compound #2 (0.3, 3.0, and 30 mg/kg) orally for 6 months. Bone mineral content was measured prior to the onset of dosing, after 3 and 6 months of treatment by dual energy X-ray absorptiometry using a XR-26 Norland instrument. The bone mineral content of the spine (AP spine) was determined using the standard AP spine analysis package supplied with the densitometer. Dogs were scanned in a anterior-posterior position at settings of 1.5×1.5 mm pixel size at a scan speed of 60 mm/sec. Duplicate AP spine mineral content measurements was taken at pretreatment, 3 months and 6 months of treatment. The duplicate determinations of BMC measurements at each time period were averaged and the 3 and 6 month data expressed as a percent change for each animal. The results are shown in TABLE 7.

TABLE 7

COMPOUND #2 ON BONE MINERAL CONTENT IN THE AP SPIKE FOLLOWING 3 AND 6 MONTHS OF TREATMENT IN THE FEMALE BEAGLE DOG

|  | VEHICLE | 0.3 MG/KG | 3.0 MG/KG | 30 MG/KG |
|---|---|---|---|---|
| MONTH 3 |  |  |  |  |
| % BASELINE | 1.0% | 3.6% | 1.5% | 3.7% |
| (95% Confid Int) | (−1.8,3.8) | (0.9,6.2) | (−1.6,4.6) | (1.0,6.4) |
| Δ VEHICLE | — | 2.6% | 1.0% | 3.2% |
| (95% Confid Int) |  | (−1.3,6.5) | (−3.7,5.7) | (−1.2,7.6) |
| P-value | — | 0.1005 | 0.7656 | 0.7505 |
| MONTH 6 |  |  |  |  |
| % BASELINE | 2.1% | 3.8% | 2.3% | 0.2% |
| (95% Confid Int) | (0.1,4.0) | (1.0,6.5) | (−0.5,5.0) | (−2.2,2.6) |
| Δ VEHICLE | — | 1.7% | 0.2% | −1.9% |
| (95% Confid Int) |  | (−1.7,5.0) | (−3.1,3.5) | (−5.0,1.2) |
| P-value | — | 0.1605 | 0.4540 | 0.8825 |

Serum osteocalcin was determined at pretreatment and at 1,2,3, and 6 months throughout the course of treatment. Adult female beagle dogs (16/treatment group) were administered either vehicle (0.5% methylcellulose, 1 ml/kg) or Compound #2 (0.3, 3.0, and 30 mg/kg) orally for 6 months. The results are shown in TABLE 8. Each value represents the mean ±S.E. of osteocalcin levels expressed as ng/ml measured in 15–16 dogs. Analyses of these data show that osteocalcin levels in the vehicle treated animals decreased from pretreatment levels over time ($p<0.05$). No change in serum osteocalcin levels over time was observed in those animals given Compound #2 at doses of 0.3 or 3.0 mg/kg/day. However, in dogs given 30 mg/kg/day of Compound #2, serum osteocalcin increased from pretreatment levels over time ($p<0.05$). When compared at individual times during the study, those dogs given 3 mg/kg of Compound #2 had higher osteocalcin levels than did the vehicle controls within 1 month. Osteocalcin levels remained elevated in this group for tile remainder of the study. Within 2 months of treatment, animals given 30 mg/kg of Compound #2 also showed osteocalcin concentrations greater than controls and this elevation continued through 6 months. Only at the 3 month time point did animals given Compound #2 at the low dose (0.3 mg/kg/day) have osteocalcin levels above control levels.

TABLE 8

COMPOUND #2 ON SERUM OSTEOCALCIN LEVELS IN THE FEMALE BEAGLE DOG

|  | VEHICLE | 0.3 MG/KG | 3.0 MG/KG | 30 MG/KG |
|---|---|---|---|---|
| Pretreatment | 31.43± 3.23 | 34.30 ± 2.65 | 36.64 ± 3.02 | 29.54 ± 2.67 |
| Month 1 | 24.12± 2.67 | 27.63 ± 2.49 | 37.12 ± 3.66* | 30.17 ± 2.69 |
| Month 2 | 27.02± 2.32 | 31.19 ± 1.89 | 38.67 ± 3.66* | 36.76 ± 2.36* |
| Month 3 | 22.79± 1.93 | 35.41 ± 2.52* | 39.21 ± 2.78* | 36.25 ± 2.51* |
| Month 6 | 25.12± 3.44 | 29.91 ± 2.34 | 35.08 ± 1.66* | 34.81 ± 2.90* |

*Value significantly greater than same-time vehicle value ($p < 0.05$).

Urinary hydroxyproline/creatinine ratios were determined at pretreatment, 3 months and 6 months of treatment. Adult female beagle dogs (16/treatment group) were administered either vehicle (0.5% methylcellulose, 1 ml/kg) or Compound #2 (0.3, 3.0, and 30 mg/kg) orally for 6 months. The results are shown in TABLE 9. Each value represents the mean ±S.E. of the hydroxyproline/creatinine expressed as ng/ml measured in 15–16 dogs. Urinary hydroxyproline/creatinine ratio were increased by Compound #2 only at the 3 month time period but not after 6 months of treatment.

COMPOUND #2 ON URINARY HYDROXYPROLINE/ CREATININE RATIO IN THE FEMALE BEAGLE DOG

|  | PRE-TREATMENT | 3 MONTHS | 6 MONTHS |
|---|---|---|---|
| VEHICLE | 31.22 + 2.84 | 27.27 + 2.15 | 38.18 + 2.99 |
| 0.3 MG/KG | 29.59 + 1.70 | 32.54 + 2.98 | 40.42 + 2.90 |
| 3.0 MG/KG | 28.97 + 2.24 | 36.58* + 2.34 | 43.32 + 2.93 |
| 30 MG/KG | 33.16 + 1.36 | 37.11* + 2.38 | 42.54 + 2.98 |

*Value significantly greater than same-time vehicle value ($p < 0.05$).

We claim:

1. A compound of formula I:

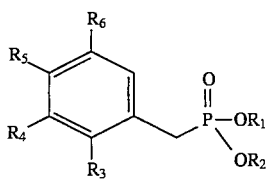

wherein $R_1$ and $R_2$ are the same or different and are selected from any of hydrogen, alkyl, alkenyl or aralkyl;

wherein $R_3$ and $R_5$ may each be either H or $CF_3$, with the proviso that only one of $R_3$ or $R_5$ may be $CF_3$ at the same time;

wherein $R_4$ and $R_6$ may each be H or $CF_3$, with the proviso that if either or both of $R_4$ and $R_6$ are $CF_3$, neither $R_3$ nor $R_5$ may be $CF_3$, with the further proviso that $R_3$–$R_6$ may not each be H at the same time, and with the further proviso that $R_1$ and $R_2$ can both be ethyl only when $R_4$ and $R_6$ are each $CF_3$; or the pharmaceutically acceptable salts thereof.

2. The compounds of claim 1, wherein each of $R_1$ and $R_2$ are H.

3. A compound of claim 1 selected from any one 3-trifluoromethylbenzyl-phosphonic acid; ethyl 3-trifluoromethylbenzylphosphonic acid; allyl ethyl 3-trifluoromethylbenzylphosphonate; diethylaminoethyl ethyl 3-trifluoromethylbenzylphosphonate and ethyl 3-phenylpropyl 3-trifluoromethylbenzylphosphonate.

4. A pharmaceutical composition comprising a compound of formula I:

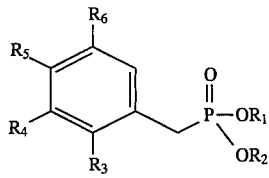

wherein $R_1$ and $R_2$ are the same or different and are selected from any of hydrogen, alkyl, alkenyl or;

wherein $R_3$ and $R_5$ may each be either H or $CF_3$, with the proviso that only one of $R_3$ or $R_5$ may be $CF_3$ at the same time;

wherein $R_4$ and $R_6$ may each be H or $CF_3$, with the proviso that if either or both of $R_4$ and $R_6$ are $CF_3$, neither $R_3$ nor $R_5$ may be $CF_3$, with the further proviso that $R_3$–$R_6$ may not each be H at the same time, and a pharmaceutically acceptable carrier, wherein the compound of formula I is present in a therapeutically effective amount.

5. A composition according to claim 4, wherein each of $R_1$ and $R_2$ is H.

6. A composition according to claim 4, wherein the compound is selected from any one of diethyl 3-trifluoromethylbenzylphosphonate; 3-trifluoromethylbenzylphosphonic acid; ethyl 3-trifluoromethylbenzylphosphonic acid; allyl ethyl 3-trifluoromethylbenzylphosphonate; diethylaminoethyl ethyl 3trifluoromethylbenzylphosphonate; and ethyl 3-phenylpropyl 3-trifluoromethylbenzylphosphonate.

7. A method of treating bone wasting diseases in mammals which comprises administering to said mammal an effective amount of compound of formula I:

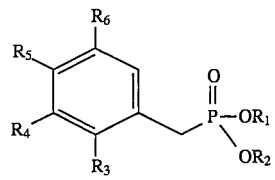

wherein $R_1$ and $R_2$ are the same or different and are selected from any of hydrogen, alkyl, alkenyl or aralkyl;

wherein $R_3$ and $R_5$ may each be either H or $CF_3$, with the proviso that only one of $R_3$ or $R_5$ may be $CF_3$ at the same time;

wherein $R_4$ and $R_6$ may each be H or $CF_3$, with the proviso that if either or both of $R_4$ and $R_6$ are $CF_3$, neither $R_3$ nor $R_5$ may be $CF_3$, with the further proviso that $R_3$–$R_6$ may not each be H at the same time, or the pharmaceutically acceptable salts thereof.

8. The method of claim 7, wherein the compound of formula I is diethyl 3-trifluoromethylbenzylophosphonate.

9. A method of treating osteoporosis in mammals which comprises administering to said mammal an effective amount of a compound of formula I:

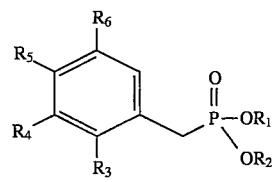

wherein $R_1$ and $R_2$ are the same or different and are selected from any of hydrogen, alkyl, alkenyl hydroxyalkyl, alkoxyalkyl, aralkyl, aryl, or aminoalkyl;

wherein $R_3$ and $R_5$ may each be either H or $CF_3$, with the proviso that only one of $R_3$ or $R_5$ may be $CF_3$ at the same time;

wherein $R_4$ and $R_6$ may each be H or $CF_3$, with the proviso that if either or both of $R_4$ and $R_6$ are $CF_3$, neither $R_3$ nor $R_5$ may be $CF_3$, with the further proviso that $R_3$–$R_6$ may not each be H at the same time, and pharmaceutically acceptable salts thereof.

10. The method of claim 9, wherein the compound of formula I is diethyl 3-trifluoromethylbenzylphosphonate.

11. The method of claim 9, wherein the compound of formula I is 3-trifluoromethylbenzylphosphonic acid.

12. The method of claim 7, wherein the compound of formula I is 3-trifluoromethylbenzylphosphonic acid.

\* \* \* \* \*